(12) United States Patent
Yoo et al.

(10) Patent No.: US 7,659,149 B2
(45) Date of Patent: Feb. 9, 2010

(54) METHOD OF ELECTRICALLY DETECTING BIOMOLECULE

(75) Inventors: Kyu-tae Yoo, Seoul (KR); Sung-ouk Jung, Suwon-si (KR); Jun-hong Min, Yongin-si (KR); Ji-na Namgoong, Yongin-si (KR); Soo-hyung Choi, Hwascong-si (KR); Jeo-young Shim, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 339 days.

(21) Appl. No.: 11/345,790

(22) Filed: Feb. 2, 2006

(65) Prior Publication Data

US 2006/0246478 A1 Nov. 2, 2006

(30) Foreign Application Priority Data

Feb. 3, 2005 (KR) .................. 10-2005-0010183

(51) Int. Cl.
*C12Q 1/68* (2006.01)
*H01L 21/66* (2006.01)
*H01L 21/00* (2006.01)
*H01L 21/336* (2006.01)
*H01L 29/80* (2006.01)

(52) U.S. Cl. ................ 438/123; 438/48; 438/49; 438/56; 438/257; 435/6; 257/256

(58) Field of Classification Search ........... 438/123, 438/48, 49, 56, 257; 435/6; 257/256
See application file for complete search history.

(56) References Cited

U.S. PATENT DOCUMENTS

| | | | | |
|---|---|---|---|---|
| 4,238,757 | A | 12/1980 | Schenck | 357/25 |
| 4,777,019 | A | 10/1988 | Dandekar | 422/68 |
| 5,466,348 | A | 11/1995 | Holm-Kennedy | 204/153.1 |
| 5,846,708 | A | 12/1998 | Hollis et al. | 435/6 |
| 6,203,981 | B1 | 3/2001 | Ackley et al. | 435/6 |
| 6,482,639 | B2 | 11/2002 | Snow et al. | 435/287.2 |
| 6,815,163 | B1 * | 11/2004 | Breslauer et al. | 435/6 |
| 2003/0027157 | A1 * | 2/2003 | Fu et al. | 435/6 |

OTHER PUBLICATIONS

Gilmour et al., Journal of Bacteriology, Dec. 2005, pp. 8196-8200.*
Stephenson et al., Current Medicinal Chemistry, 2004, vol. 11, pp. 765-773.*
Kim et al., Japanese Journal of Applied Physics. vol. 43(6B): 3855-3859; 2004.*

* cited by examiner

*Primary Examiner*—Sue Liu
(74) *Attorney, Agent, or Firm*—Cantor Colburn LLP (57) ABSTRACT

Provided is a method of sensing biomolecules using a bioFET, the method including: forming a layer including Au on a gate of the bioFET; forming a probe immobilized on a substrate separated from the gate by a predetermined distance, and a biomolecule having a thiol group (—SH) which is incompletely bonded to the probe; reacting the probe with a sample including a target molecule; and measuring a current flowing in a channel region between a source and a drain of the bioFET.

3 Claims, 5 Drawing Sheets

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: probe DNA

<400> SEQUENCE: 1
atgacaatga gtatgccta                                              19

<210> SEQ ID NO 2
<211> LENGTH: 15
<212> TYPE: DNA
<213> ORGANISM: Artificial Sequence
<220> FEATURE:
<223> OTHER INFORMATION: probe DNA

<400> SEQUENCE: 2
taggcatact cattg                                                  15

<210> SEQ ID NO 3

```
-continued

<211> LENGTH: 19
<212> TYPE: DNA
<213> ORGANISM: Artificial Sequence
<220> FEATURE:
<223> OTHER INFORMATION: target DNA

<400> SEQUENCE: 3
taggcatact cattgtcat                                               19

<210> SEQ ID NO 4
<211> LENGTH: 15
<212> TYPE: DNA
<213> ORGANISM: Artificial Sequence
<220> FEATURE:
<223> OTHER INFORMATION: mismatch target DNA

<400> SEQUENCE: 4
tgttctcttg tcttg                                                   15

<210> SEQ ID NO 5
<211> LENGTH: 19
<212> TYPE: DNA
<213> ORGANISM: Artificial Sequence
<220> FEATURE:
<223> OTHER INFORMATION: probe DNA

<400> SEQUENCE: 5
atgacaatga gtatgccta                                               19

<210> SEQ ID NO 6
<211> LENGTH: 19
<212> TYPE: DNA
<213> ORGANISM: Artificial Sequence
<220> FEATURE:
<223> OTHER INFORMATION: target DNA

<400> SEQUENCE: 6
taggcatact cattgtcat                                               19
```

METHOD OF ELECTRICALLY DETECTING BIOMOLECULE

CROSS-REFERENCE TO RELATED PATENT APPLICATIONS

This application claims the benefit of Korean Patent Application No. 10-2005-0010183, filed on Feb. 3, 2005, in the Korean Intellectual Property Office, the disclosure of which is incorporated herein in its entirety by reference.

BACKGROUND OF THE INVENTION

1. Field of the Invention

The present invention relates to a method of detecting a biomolecule using a field effect transistor (FET), and more particularly, to a method of electrically sensing a bond between a probe biomolecule and a target biomolecule.

2. Description of the Related Art

Biosensors, which include transistors, are sensors that electrically sense biomolecules. Biosensors are manufactured using semiconductor processes, quickly convert electric signals, and can be easily applied to integrated circuits (ICs) and MEMS. Due to these advantages, much research has gone into biosensors.

U.S. Pat. No. 4,238,757 was the first Patent regarding the detection of biological reactions using a FET, and is directed to a biosensor capable of identifying an antigen-antibody reaction by detecting a current that varies due to a change in the surface charge concentration of a semiconductor inversion layer. This patent is directed toward a biosensor for sensing proteins. In U.S. Pat. No. 4,777,019 biological monomers are adsorbed onto the surface of a gate, and hybridization between the biological monomers and complementary monomers is measured using a FET. U.S. Pat. No. 5,846,708 discloses a method of sensing hybridization using a charged coupled device (CCD). In this method, the hybridization can be identified using a phenomenon that bonded biomolecules absorb light. In U.S. Pat. Nos. 5,466,348 and 6,203,981, a TFT is used and a S/N ratio is improved by application to a circuit.

A thin film transistor (TFT) has lower manufacturing costs than a transistor formed on a silicon substrate, and a TFT enables the formation of an array-type chip with increased integrity by increasing the area of a substrate. An FET used as a biosensor has lower costs and requires less time than other conventional methods. In addition, an FET can be easily applied to integrated circuit (IC)/MEMS processes.

Figure 1A:
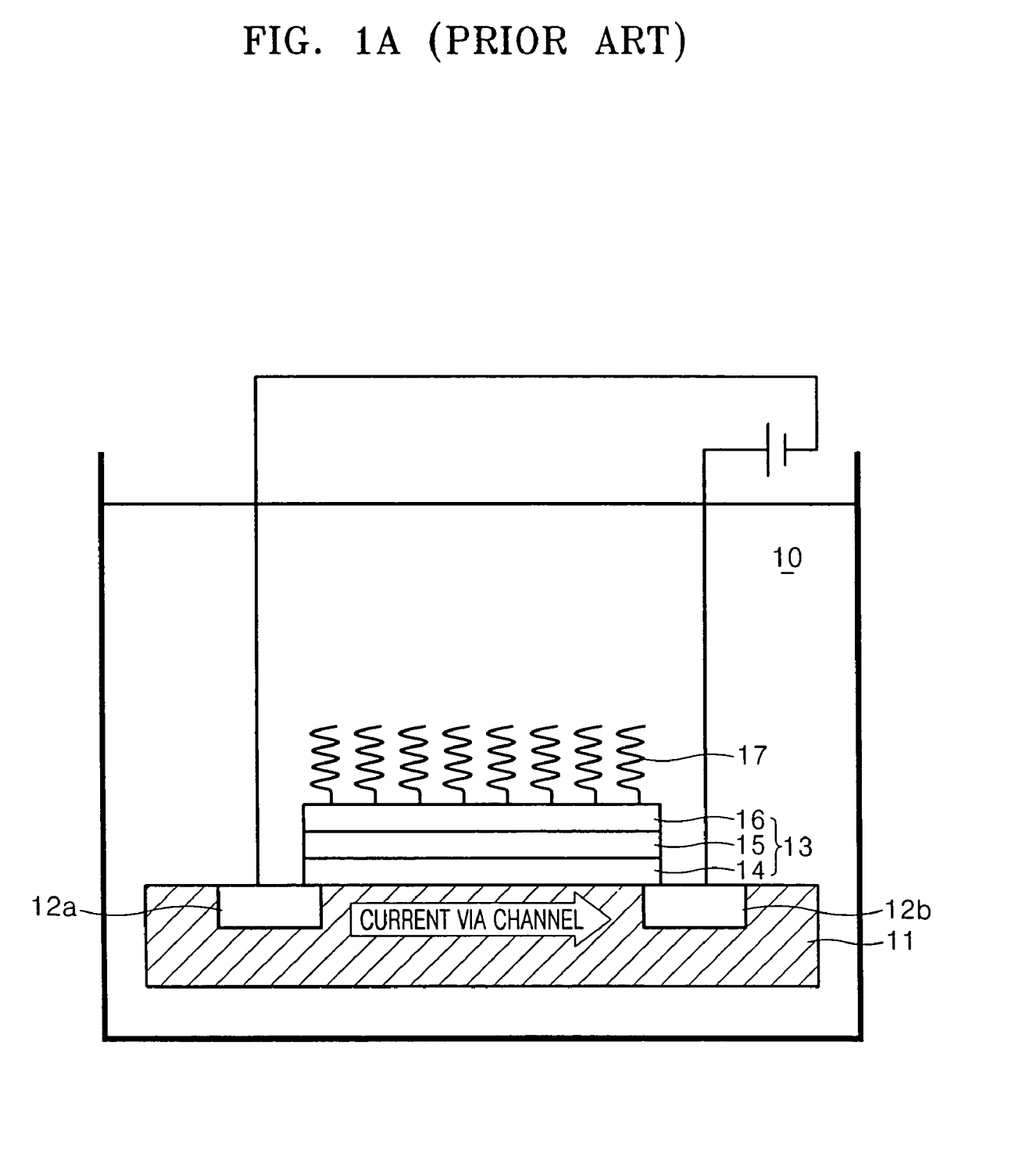
FIG. 1A is a sectional view of a typical bio field effect transistor (FET)

FIG. 1 is a sectional view of a typical bioFET. Referring to FIG. 1, a source 12a and a drain 12b are respectively formed in side portions of a substrate 11 doped with an n- or p-type material. The source 12a and the drain 12b are of an opposite conductivity type to the substrate 11. A gate 13 contacting the source 12a and the drain 12b is formed on the substrate 11. The gate 13 typically includes an oxidized layer 14, a poly silicon layer 15, and a metal layer 16. A probe biomolecule 17 is bonded to the metal layer 16 of the gate 13. When a predetermined target biomolecule is bonded to the probe biomolecule 17 by, for example, hydrogen bonding, the current changes. The change in the current is measured and the bonding of the probe biomolecule 17 and the predetermined target biomolecule can be identified.

The above-described conventional techniques, however, cannot retain reliable accuracy and be reliably reproduced when charged biomolecules are sensed in an electrolyte 10. In detail, the target biomolecule is bonded to the probe biomolecule 17 immobilized on the surface of the gate 13 in an electrolyte of a bioFET. At this time, when charged biomolecules are separated from the surface of the gate 13 by a debye length or farther, the charged biomolecules cannot affect an electric potential at the surface of the gate 13 due to ionic shielding of ions adjacent to biomolecules in the electrolyte 10, and it is difficult to accurately measure the electrical potential of the surface of the gate 13. Accordingly, the detection of immobilization of the probe biomolecule 17 to the surface of the gate 13 and hybridization of the probe biomolecule 17 with the target biomolecule has low reproducibility and accuracy.

In order to prevent ionic shielding, ionic concentration of the electrolyte can be decreased to increase the debye length. However, when the ionic concentration is decreased, for example, when the concentration of NaCl is 0.01 M or less, the detection efficiency decreases.

U.S. Pat. No. 5,466,348 discloses an apparatus for sensing biomolecules in a dry environment to prevent ion shielding. However, practical use of the apparatus is limited and a separate apparatus is required.

In U.S. Pat. No. 6,203,981, two transistor are used to decrease noise, and thus, increase the S/N ratio. However, desired effects of signal amplification cannot be obtained.

In U.S. Pat. No. 6,482,639 B2, charged biomolecules and uncharged biomoleclues are detected through a change in capacitance due to adsorption/bonding of biomolecules between a reference electrode and a gate surface. However, reproducibility and accuracy for sensing using a bioFET are not reliable.

SUMMARY OF THE INVENTION

The present invention provides a method of detecting biomolecules using a bio field effect transistor (FET). By using the method, the hybridization of a probe biomolecule with a target biomolecule at the surface of a bioFET can be accurately detected and high signal amplification can be obtained.

According to an aspect of the present invention, there is provided a method of sensing biomolecules in an electrolyte using a bio field effect transistor (FET), the method including: (a) forming a layer comprising Au on a gate of the bioFET; (b) forming a probe immobilized to a substrate separated from the gate by a predetermined distance, and a biomolecule having a thiol group (—SH), which is incompletely bonded to the probe; (c) reacting the probe with a sample including a target molecule; and (d) measuring a current flowing in a channel region between a source and a drain of the bioFET.

The biomolecule, the probe, or the target may be DNA, RNA, or a protein.

A bonding force between the probe and the target molecule may be greater than a bonding force between the probe and the thiol group-containing biomolecule.

In operation (c), the biomolecule may be separated from the probe when the target molecule is bonded to the probe.

In operation (d), the flow of the current may be formed by bonding of the thiol group of the biomolecule with Au on the surface of the gate.

The incomplete bonding in operation (b) may be formed by the biomolecule whose bonding force with the probe is weaker than the bonding force between the probe and the target biomolecule.

According to another aspect of the present invention, there is provided a method of sensing biomolecules in an electrolyte using a bioFET, the method including: (a) immobilizing a first probe to a layer comprising Au on a gate of the bioFET; (b) supplying a second probe to which a liposome containing a thiol group (—SH) compound is bonded; (c) reacting a target molecule-containing sample with the first probe and the second probe, and then washing the result; (d) bursting the liposome; and (e) measuring a current flowing in a channel region between a source and a drain of the bioFET.

The first probe, the second probe, or the target is DNA, RNA, or a protein.

A portion of the target may complementarily correspond to the first probe and another portion of the target may complementarily correspond to the second probe.

The thiol group compound may be any compound having a thiol group, and may be mercaptohexanol or cysteine. In addition, the thiol group compound may be any compound including an anionic molecule, and may be aspartate or glutamate.

The burst of the liposome in operation (d) can be made using any methods, preferably, using the difference of osmotic pressure.

The flow of the current in operation (e) may be generated by bonding of a thiol group, which is released by the burst of the liposome in operation (d), with Au formed on the surface of the gate.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

A basic principle of the present invention will now be described.

Figure 1B:
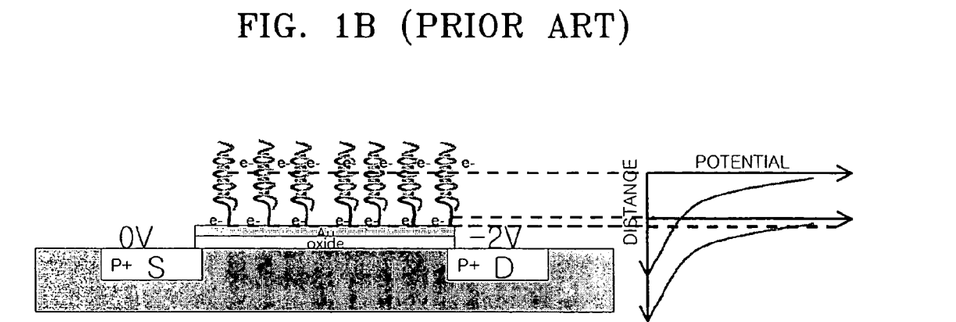
FIG. 1B illustrates the structure and debye length of a typical bioFET.
Figure 1C:
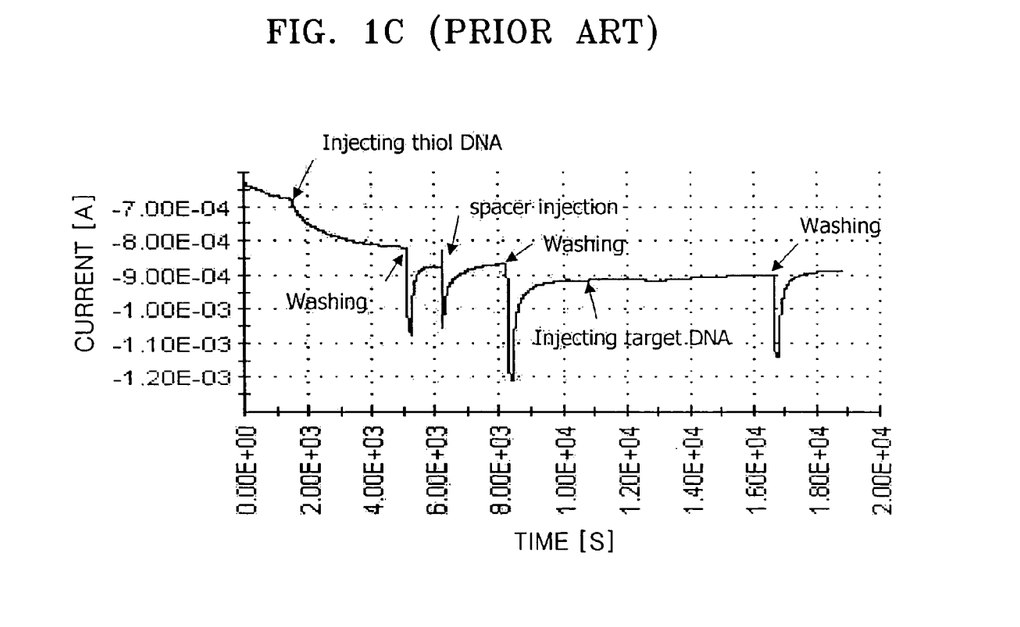
FIG. 1C is a graph of the drain current change of the bioFET of FIG. 1B measured using a Kethley 4200.

FIGS. 1A through 1C relate to a conventional bio field effect transistor (FET). Referring to FIG. 1A, a probe DNA 17 is immobilized on a gate 13 of a bioFET installed in an electrolyte 10. A source 12a and a drain 12b, which are composed of a predetermined material, are formed on side portions of a substrate 11, respectively. The gate 13 contacts the source 12a and the drain 12b and is formed on the substrate 11. Although the structure of the gate 13 is not limited, the gate 13 generally includes a gate insulating layer 14, a gate electrode layer 15, and a metal material layer 16, to which the probe DNA 17 is immobilized.

When the DNA immobilizes on the surface of the gate 13 of the bioFET, the surface charge density changes, and thus, a current flowing in a channel region of the substrate 11 is changed. Immobilization of the probe DNA 17 and hybridization of a target and the probe DNA 17 can be detected according to the change in the current.

Referring to FIG. 1A, probe biomolecules, for example, probe DNAs 17, are charged and immobilized on the substrate 11. As the number of immobilized probe DNAs 17 increases, the surface charge density increases, and thus, more current flows in the channel between the source 12a and the drain 12b. Potential damping of charged biomolecules due to ionic shielding in the electrolyte 10 is dependent on the debye length. That is, the degree to which the bioFET channel region is effectively affected may vary according to the debye length of immobilized or hybridized charged biomolecules.

The entire surface of a typical FET, excluding the gate 13, is subjected to passivation to prevent ionic diffusion in the electrolyte 10. The gate 13 is coated with, for example, Au 16, and the probe DNA 17 is modified to have a thiol group. In this case, the thiol group of the probe DNA 17 is bonded to the Au 16 by self-assembly so that the probe DNA 17 is immobilized on the gate 13.

When the probe DNA 17 with the thiol group is immobilized on the Au 16 of the gate 13 and when the probe DNA 17 immobilized on the surface of the gate 13 is hybridized with a target molecule, the immobilization and hybridization directly affect a current flowing in the channel region between the source 12a and the drain 12b when a predetermined voltage is applied between the source 12a and drain 12b of the bioFET in the electrolyte 10.

However, based on the finding by the present inventors, as illustrated in FIGS. 1B and 1C, when the Au 16 is bonded to the thiol group of the probe DNA 17, the bonding occurs in the vicinity of the gate 13, and thus, the debye length does not affect the current flowing in the channel between the source 12a and drain 12b and the change in the current is very large. On the other hand, the hybridization between the probe DNA 17 and the target molecule occurs away from the gate. As a result, the current is proportional to the negative exponential of the distance between the surface of the gate 13 and a point where the hybridization occurs. As a result, the change in the current when hybridization occurs is comparatively smaller than the change in the current when the bonding between the Au 16 and the thiol group occurs. As illustrated in FIG. 1C, when Au 16 is bonded to the thiol group of the probe DNA 17, the change in the current is 202 μA, but when the probe DNA 17 is hybridized with the target molecule, the change in the current is as little as 25 μA. That is, the signal resulting from the hybridization is very weak and a S/N ratio is too small.

In order to solve this problem, the present inventors developed a sensing method in which a large increase of the current can be obtained when a probe molecule is hybridized with a target molecule. That is, in embodiments of the present invention, the bonding of Au and a thiol group, which can induce a dramatic change in the current, is controlled according to the hybridization between the target molecule and the probe.

A method of sensing biomolecules in an electrolyte using a bioFET according to a first embodiment of the present invention includes forming a layer including Au on a gate of the bioFET; forming a probe immobilized to a substrate separated from the gate by a predetermined distance, and a biomolecule having a thiol group (—SH) which is incompletely bonded to the probe; reacting the probe with a sample including a target molecule; and measuring a current flowing in a channel region between a source and a drain of the bioFET.

The sensing method according to the present embodiment will now be described in detail with reference to FIG. 2.

In a conventional method, when a bond between a probe (containing —SH) and a target molecule is induced after the probe is immobilized on the surface of a gate (Au), the change in the current is much lower when the target molecule is hybridized than when the probe is immobilized. In order to solve this problem, in the present embodiment, a probe 28 is immobilized on a substrate 31 separated from a gate 23, and a biomolecule 27 having a thiol group (—SH) is incompletely bonded to the probe 28. The term 'incomplete bonding' indicates a relatively weak bond. For example, as for complementary bonding of DNA chains, 'incomplete bonding' indicates bonding, such as mismatch, that is not complete complementary bonding. An example of DNA enabling such incomplete bonding is a DNA chain having a thiol group that is shorter than a target.

When the sample including the target is added to the bioFET in which the biomolecule 27 is incompletely bonded to the probe 28, the biomolecule 27 having the thiol group (—SH) which is incompletely bonded to the probe 28 is separated from the probe 28, and the target, which can relatively completely bind (for example, complete complementary bonding for DNA) to the probe 28, is competitively bonded to the probe 28 instead of the thiol group (—SH). Such a replacement by the target can occur because the bonding force between the target and the probe is much stronger than the bonding force between the probe and the thiol group (—SH).

The biomolecule 27, which includes thiol group, is bonded to Au 26 of the gate 23, and thus, the current flowing in a channel between a source 22a and a drain 22b changes dramatically. As a result, hybridization between the target and the probe 28 can be sensed.

In the above method, the probe, the target, or the biomolecule may be DNA, RNA, or a protein. The protein can be any biomolecule, such as an antigen, an antibody, a substrate protein, an enzyme, a coenzyme, or the like.

The bonding to the probe 28 can be any biomolecule bonding known in the art, such as nucleic hybridization, an antigen-antibody reaction, an enzyme bonding reaction, and the like.

A method of sensing biomolecules in an electrolyte using a bioFET according to a second embodiment of the present invention includes immobilizing a first probe to a layer comprising Au on a gate of the bioFET; supplying a second probe to which a liposome containing a thiol group (—SH) compound is bonded; reacting a target molecule-containing sample with the first probe and the second probe, and then washing the result; bursting the liposome; and measuring a current flowing in a channel region between a source and drain of the bioFET.

The present embodiment will now be described in detail with reference to FIG. 3.

According to the present embodiment, first, a first probe 28 is immobilized on the surface of a gate (Au). The immobilizing method is not limited and any method known in the art can be used.

Then, a second probe 29 to which a liposome 30 is bonded is added to an electrolyte in which reactions occur. The liposome 30 includes a compound including a thiol group (—SH). Such a thiol group-containing compound can be any compound having the thiol group, such as mercaptohexane or cysteine. In addition, the thiol group-containing compound can be a compound having an anionic molecule. The compound having an anionic molecule can be aspartate or glutamate.

A sample including a target is added to the bioFET. As a result, the target is reacted with the first probe 28 and the second probe 29 so that the target is bonded to the first probe 28 and the second probe 29. After the bonding occurs, washing is performed to remove non-bound probes.

Thereafter, the liposome 30 is burst to release the compound having the thiol group. The released thiol group is bonded to Au of the gate 23, and thus, a current flows in the channel region between a source 22a and a drain 22b. As a result, hybridization between the target and the probes 28 and 29 can be sensed.

As described above, since the bonding of Au and —SH, which generates strong electrical signals, can occurred according to the hybridization of a target and a probe and the amount of the hybridized target, more accurate sensing can be achieved.

The present invention will now be described in further detail with reference to the following examples. These examples are for illustrative purposes only and are not intended to limit the scope of the present invention.

EXAMPLES

Example 1

Immobilization of DNA Probe and Hybridization Between DNA Probe and Target DNA

1. Immobilization of DNA Probe

Figure 2:
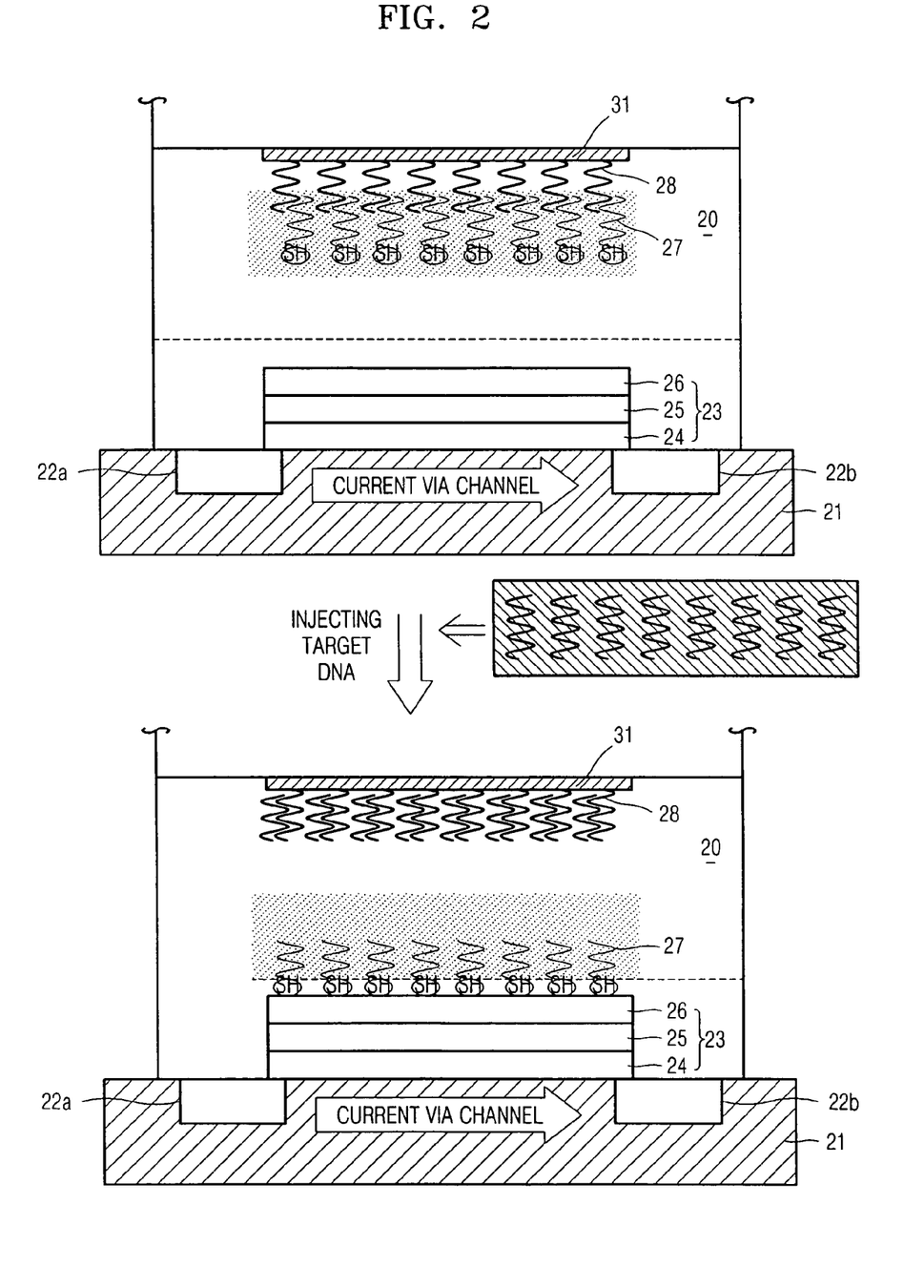
FIG. 2 illustrates a method according to an embodiment of the present invention.

As illustrated in FIG. 2, a gate 23 including an oxidized layer 24, a polysilicon layer 25, and a metal layer (Au layer); a p-channel bioFET was used; and a reference bioFET that did not include the metal layer (Au layer) on the gate was used so that biomolecules were not immobilized.

First, ɣ-aminopropyltrietoxysilane (GAPS) was coated on a silicon oxide pad of a silicon substrate chip 31, and a DNA having an amino group at its 5'-end was immobilized thereon.

That is, after GAPS was spin coated on the substrate 31, a 20 µM probe polynucleotide having an aminohexyl group at its 5'-end (5'-ATGACAATGAGTATGCCTA-3') (SEQ ID No. 1), which was dissolved in 6 mM PEG (Aldrich Co., molecular weight of 10,000) in a 0.1 M $NaHCO_3$ pH 9 solution containing 50% DMSO, was reacted with the GAPS film to achieve immobilization of the probe.

After the probe was immobilized, the probe was hybridized with a DNA that was modified to complementarily correspond to a portion of the probe and had a thiol group (hereinafter, referred to as 'a hurdle DNA' (5'-SH-TAGGCATACT-CATTG-3') (SEQ ID No. 2). Since the bioFET in another channel was blocked through a valve, the attachment of the modified hurdle DNA containing a thiol group to the surface of the gate of the bioFET could be prevented. After the hybridization, non-hybridized hurdle DNAs that were not reacted with the probe were removed by washing.

2. Hybridization of Probe and Target DNA

The valve between a micro channel including the silicon oxide pad to which the probe was immobilized and a micro channel including the bioFET and the reference bioFET were opened such that the micro channels were connected to each other, and then a 1 µM target DNA (5'-TAG GCA TAC TCA TTGTCAT-3') (SEQ ID No. 3) was added thereto.

3. Hybridization of Probe and Mismatch Target

The valve between a micro channel including the silicon oxide pad to which the probe was immobilized and a micro channel including the bioFET and a reference bioFET were opened such that these micro channel were connected to each other, and then a 1 µM mismatch target DNA (5'-TGT TCT CTT GTC TTG-3') (SEQ ID No. 4) was added thereto.

4. Measurement Method

A voltage was applied to the bioFET and the change in current was measured using a Kiethley 4200 parameter analyzer. −2V was applied to the gate through a standard electrode and −2V was applied between a source and a drain, and the current between the drain and source was measured.

The above processes 1 through 4 were repeated three times. The results are shown in Table 1.

TABLE 1

|  | Mismatch Injection | Perfect Match Injection |
|---|---|---|
| Experiment 1 | 11 µA | 20 µA |
| Experiment 2 | 2 µA | 25 µA |
| Experiment 3 | 32 µA | 60 µA |

Figure 4:
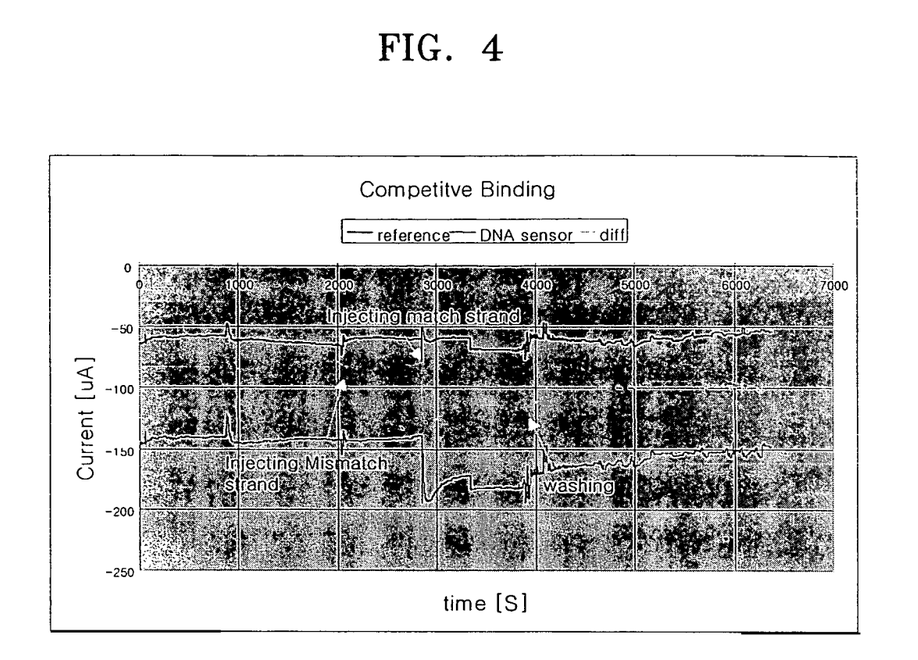
FIG. 4 is a graph of current flowing in a channel between a source and a drain when a target is detected using the method illustrated in FIG. 2.

The average value of the results obtained from the three experiments is shown in FIG. 4. In this case, each chip included the bioFET and the reference bioFET, which did not include a metal layer (Au layer) on the surface of the gate. Since the reference bioFET did not include the Au layer, the DNA having the thiol group was not immobilized thereon. Referring to FIG. 4, for the reference bioFET, the addition of the mismatch DNA and the target DNA resulted in a small change in the current. However, for the bio FET including the Au layer, the addition of the mismatch DNA resulted in a small current change while the addition of the match target DNA resulted in an increase of about 20 µA or more in the current.

Example 2

Sensing Method Using Liposome

1. Immobilization of DNA Probe

Figure 3:
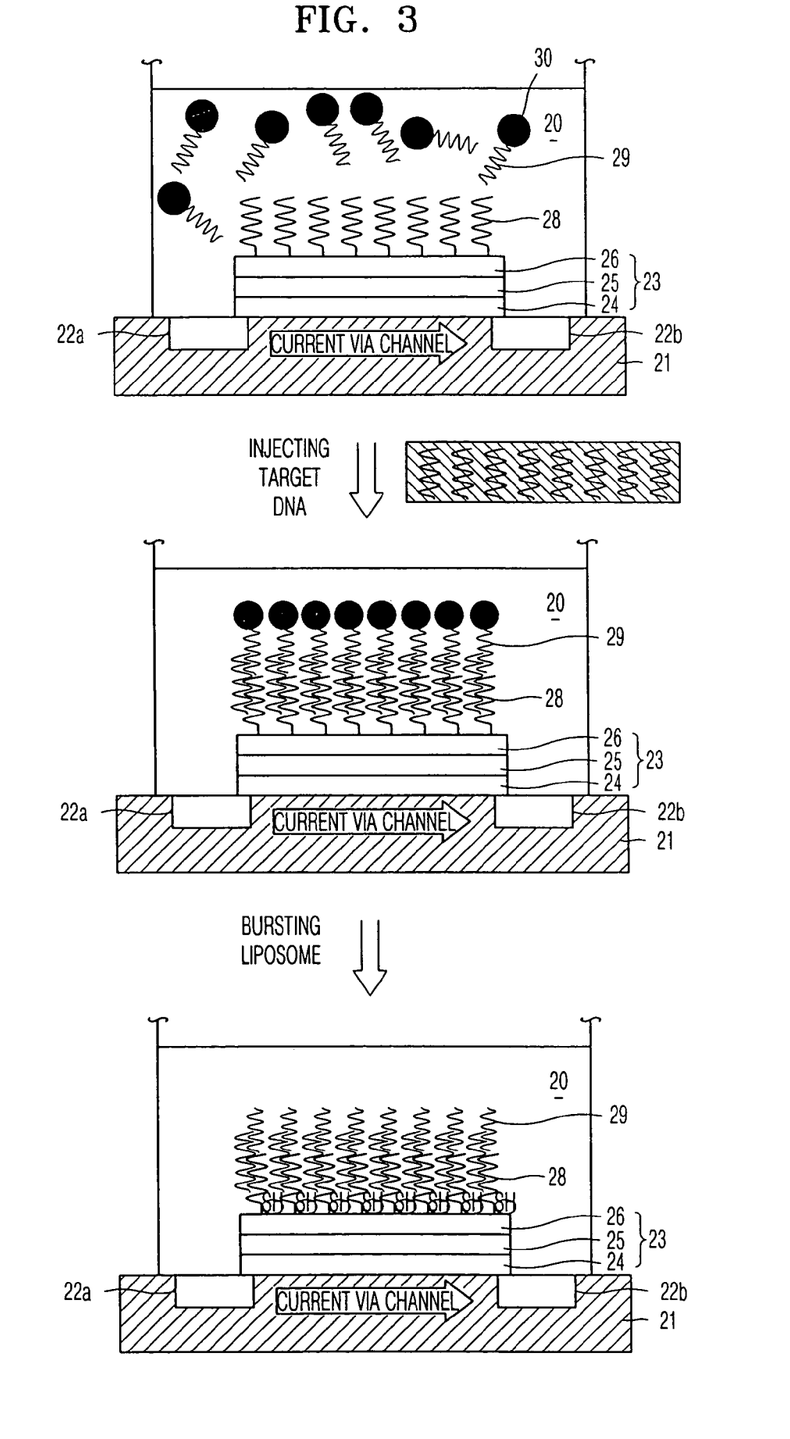
FIG. 3 illustrates a method according to another embodiment of the present invention.

As illustrated in FIG. 3, a gate 23 was formed on an oxidized layer 24, a polysilicon layer 25, and a metal layer (Au layer); a p-channel bioFET was used; and a reference bioFET that did not include a metal layer (Au layer) on a gate was used so that biomolecules were not immobilized.

A thiol-modified probe DNA (5'-SH-ATGACAATGAG-TATGCCTA-3') (SEQ ID No. 5) was immobilized on the Au layer, the surface of the gate, using a self assembly monolayer (SAM) method.

2. Hybridization of Probe and Target DNA

A target gene having a liposome-epoxy at its 5' end (liposome-epoxy-$NH_2$-TAG GCA TAC TCA TTGTCAT-3') (SEQ ID No. 6) was injected to the bioFET. The liposome included mercaptohexanol (MCH).

The target gene was reacted with a probe DNA at 40° C. for 3 hours so that the target gene was hybridized with the probe DNA.

3. Burst of Liposome

The liposome was burst by adding methanol.

Thereafter, the current was measured in the same manner as in Example 1. The results are shown in FIG. 5.

Figure 5:
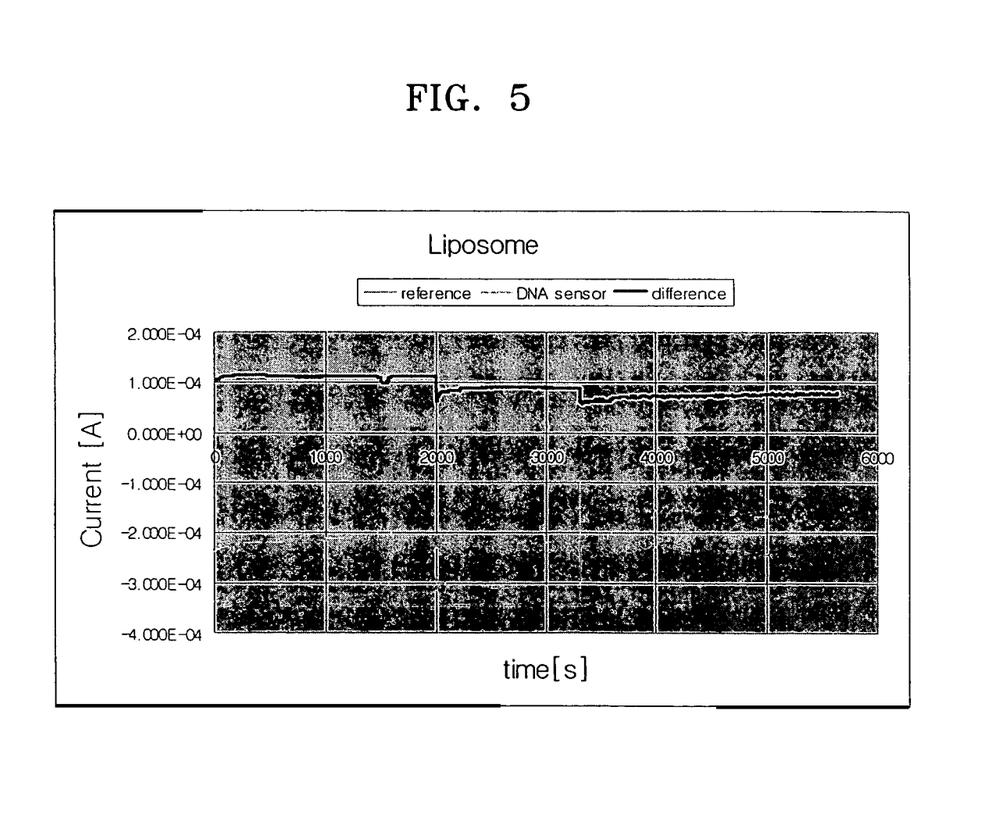
FIG. 5 is a graph of current flowing in a channel between a source and a drain when a target is detected using the method illustrated in FIG. 3.

As shown in FIG. 5, the change in the current occurred when an amine-modified match target gene connected to a liposome-epoxy including mercaptohexnol was hybridized with an immobilized probe gene and then the liposome was burst to release mercaptohexanol. That is, the target gene connected to the liposome was added and then methanol was added to burst the liposome. In this case, the current was increased by about 40 µA.

Based on the above experimental results, it was determined that the liposome could be bonded to a second probe, instead of a target, and then, the target could be added. When this was performed, a sandwich-shaped bond was formed, as shown in FIG. 3. The liposome was burst by the variation in osmotic pressures, and the change in the current was measured. As a result, the presence of a target gene was identified.

A method of sensing biomolecules in an electrolyte using a bioFET has high signal amplification and a high S/N ratio so that excellent reproducibility and accuracy can be attained.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of sensing a target nucleic acid in an electrolyte using a bio field effect transistor (FET), the method comprising:
   (a) forming a layer comprising Au on a gate of a bio field effect transistor (bioFET);
   (b) bonding a nucleic acid having a thiol group (—SH) to a probe nucleic acid immobilized on a substrate separated from the gate by a predetermined distance, wherein the nucleic acid having a thiol group is incompletely bonded to the probe nucleic acid;
   (c) contacting the probe nucleic acid with a sample including a target nucleic acid,
   wherein a bonding force between the probe nucleic acid and the target nucleic acid is greater than a bonding force between the probe nucleic acid and the nucleic acid having a thiol group;
   (d) separating the nucleic acid having a thiol group from the probe nucleic acid by bonding the target nucleic acid to the probe;
   (e) bonding the thiol group of the nucleic acid having a thiol group with Au on the gate and
   (f) measuring a current flowing in a channel region between a source and a drain of the bioFET.

2. The method of claim 1, wherein the probe nucleic acid or the target nucleic acid is DNA or RNA.

3. The method of claim 1, wherein the nucleic acid having a thiol group is DNA or RNA.

* * * * *